(12) United States Patent
Gregson et al.

(10) Patent No.: US 8,828,441 B2
(45) Date of Patent: Sep. 9, 2014

(54) ACTIVE INGREDIENT DELIVERY SYSTEM

(75) Inventors: Christopher Gregson, Princeton, NJ (US); Matthew Sillick, Plainsboro, NJ (US)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/509,901

(22) PCT Filed: Dec. 20, 2010

(86) PCT No.: PCT/IB2010/055938
§ 371 (c)(1),
(2), (4) Date: May 15, 2012

(87) PCT Pub. No.: WO2011/077347
PCT Pub. Date: Jun. 30, 2011

(65) Prior Publication Data
US 2012/0282312 A1 Nov. 8, 2012

Related U.S. Application Data

(60) Provisional application No. 61/288,921, filed on Dec. 22, 2009.

(30) Foreign Application Priority Data

Dec. 24, 2009 (EP) .................................. 09180719

(51) Int. Cl.
| | | |
|---|---|---|
| A23L 1/00 | (2006.01) | |
| A23L 1/025 | (2006.01) | |
| A23L 1/09 | (2006.01) | |
| A23L 1/22 | (2006.01) | |
| A23G 4/06 | (2006.01) | |
| A23G 4/20 | (2006.01) | |
| A61K 8/04 | (2006.01) | |
| A61K 9/16 | (2006.01) | |

(52) U.S. Cl.
CPC .......... *A23L 1/0017* (2013.01); *A23V 2002/00* (2013.01); *A23G 4/06* (2013.01); *A23L 1/22016* (2013.01); *A23L 1/0029* (2013.01); *A23L 1/097* (2013.01); *A23V 2250/6418* (2013.01); *A23G 4/20* (2013.01); *A61K 9/1623* (2013.01); *A23L 1/22008* (2013.01)
USPC ............. 424/489; 424/401; 424/439; 424/48; 424/49; 424/515; 426/548; 514/772

(58) Field of Classification Search
CPC .......... A23G 4/06; A23G 4/20; A23L 1/0017; A23L 1/0029; A23L 1/097; A23L 1/22008; A23L 1/22016; A23V 2002/00; A23V 2250/6418; A61K 9/1623
See application file for complete search history.

(56) References Cited

U.S. PATENT DOCUMENTS

| | | | |
|---|---|---|---|
| 2,566,410 A | 9/1951 | Griffin | 424/74 |
| 2,904,440 A | 9/1959 | Dimick et al. | 426/650 |
| 3,314,803 A | 4/1967 | Dame, Jr. | 426/97 |
| 3,341,415 A | 9/1967 | Scott | 426/465 |
| 3,970,766 A * | 7/1976 | Mitchell et al. | 426/534 |
| 4,338,350 A | 7/1982 | Chen et al. | 426/658 |
| 4,388,328 A | 6/1983 | Glass | 426/3 |
| 5,075,291 A | 12/1991 | DuRoss | 514/60 |
| 5,370,881 A * | 12/1994 | Fuisz | 426/5 |
| 5,525,367 A | 6/1996 | King et al. | 426/533 |
| 6,083,438 A | 7/2000 | Gonze et al. | 264/115 |
| 6,541,034 B1 | 4/2003 | Gergely et al. | 424/490 |
| 6,875,460 B2 * | 4/2005 | Cunningham et al. | 426/548 |
| 2009/0142401 A1 | 6/2009 | Appel et al. | 424/489 |
| 2011/0027372 A1 | 2/2011 | Appel et al. | 424/489 |

FOREIGN PATENT DOCUMENTS

| | | |
|---|---|---|
| EP | 0 497 439 A1 | 8/1992 |
| EP | 1 013 176 A1 | 6/2000 |

OTHER PUBLICATIONS

Huang et al., Micro/Nanoencapsulation of Active Food Ingredients, Chapter 14, ACS Symposium Series, American Chemical Society pp. 213-232 (Mar. 2009).*
International Search Report and Written Opinion, application No. PCT/IB2010/055938, mailed Jun. 28, 2011.
Andrade et al., "Characterization of Encapsulated Flavor Systems by NIR and Low-field TD-NMR: A Chemometric Approach," Food Biophysics, 3:33-47 (Jan. 2008).
Awad et al., "A New Generation of Sucrose Products Made by Cocrystallization," Food Technology, 47(1):146-148 (Jan. 1993).
Beristain et al., "Encapsulation of Orange Peel Oil by Co-crystallization," LWT—Food Science and Technology, 29(7):645-647 (Nov. 1996).
Chen, "Ingredient technology by the sugar cocrystallization process," International Sugar Journal, 96(1152):493-496 (1994).
Cölfen et al., "Mesocrystals: Inorganic Superstructures Made by Highly Parallel Crystallization and Controlled Alignment," Agnew. Chem. Int. Ed., 44(35):5576-5591 (Sep. 2005).

(Continued)

*Primary Examiner* — Kortney L Klinkel
*Assistant Examiner* — Lisbeth C Robinson

(57) ABSTRACT

A spray-chilled particulate delivery system that has a crystalline matrix structure and includes a volatile hydrophobic active ingredient and a carrier material of erythritol, mannitol and mixtures thereof 75% or more of the carrier material, relative to the total weight of the carrier material, is in crystalline form. The system is prepared by a process that includes the steps of forming a melt of the carrier material, incorporating a volatile hydrophobic active ingredient into the melt, forming a melt-mixture comprising an emulsion, dispersion or suspension of the volatile hydrophobic active ingredient in the melt, forming discrete particles of the melt mixture, and cooling the discrete particles.

4 Claims, No Drawings

(56) References Cited

OTHER PUBLICATIONS

LaBarge, "The Search for a Low-Caloric Oil," Food Technology, 42:84-90 (Jan. 1988).

Madene et al., "Flavour encapsulation and controlled release—a review," International Journal of Food Science and Technology, 41(1):1-21 (Jan. 2006).

Sztatisz et al., "Thermal Investigations of the Crystallization of Sorbitol," Journal of Thermal Analysis, 12(3):351-360 (Jan. 1977).

Zeller et al., "Trends in development of porous carbohydrate food ingredients for use in flavor encapsulation," Trends in Food Science & Technology, 9:389-394 (Nov. 1999).

* cited by examiner

ACTIVE INGREDIENT DELIVERY SYSTEM

This application is a 371 filing of International Patent Application PCT/IB2010/055938, filed Dec. 20, 2010 and claims the benefit of U.S. application No. 61/288,921 filed Dec. 22, 2009.

TECHNICAL FIELD

The present invention relates to a delivery system for active ingredients. It also relates to a process for preparing such a delivery system.

BACKGROUND AND PRIOR ART

Delivery systems or encapsulation systems are used in various industries to protect active ingredients or to control their release. For instance, in the food industry they are often used to protect flavors, in particular against losses of liquid or volatile components (i) during storage prior to incorporation into the food products, (ii) during mixing of the flavor component with the other food ingredients, (iii) during food processing, such as cooking and baking, (iv) during transportation and storage and (v) during the preparation of the food product by the end-consumer.

Similarly, in the nutraceutical industry, they are often used to protect oxygen-sensitive active material, such as fish oils rich in polyunsaturated fatty acids, by providing an oxygen barrier around the material.

In the flavor and fragrance industry it is known to encapsulate flavors and perfumes so that their release can be controlled according to the needs of the end application.

In all of these applications, the delivery system has the primary object of protecting the sensitive liquid or volatile active ingredient against, for instance, evaporation, degradation or migration, or delaying the release rate of the active ingredient into a desired medium.

Various delivery systems are known that achieve one or more of these object, such as extruded granular delivery systems, for instance. Extruded systems are often formed by melt-extrusion and typically comprise a matrix material or carrier material for a material, product or ingredient that is encapsulated. The matrix material is often described as "viscous" or "rubbery" during the extrusion process and "glassy" in the finished product.

It is recognised by many experts in the field that, in the glassy state, all molecular translation is halted and it is this which provides effective entrapping of the flavor volatiles and prevention of other chemical events such as oxidation. Conversely, in the viscous state, the encapsulation of materials, products and ingredients is less effective in preventing leakage of the encapsulated material.

Thus, glassy matrices have to be produced very carefully to achieve the desired properties.

As an alternative to glassy matrices, it is known to encapsulate active ingredients using crystalline matrices. A well documented process for crystalline encapsulation is co-crystallisation in which an active ingredient becomes embedded in a agglomerate of macro- or microscopic crystals. Numerous publications describing this technology exist, such as Zeller et al., Trends in Food Science & Technology 9 (1999) 389-94; Madene et al. International Journal of Food Science & technology 41 (2006) 1-21); Food Technology, 47, 146-148 (1993); Food Technology, 42, 87-90. 1988; and International Sugar Journal, 96, 493-494. 1994.

U.S. Pat. No. 4,338,350 (Chen et al) describes co-crystallization and refers to concentrating a sucrose solution to the range of 95 to 97%, cooling slightly to create a supersaturated solution, mixing in a second active ingredient (such as a flavor oil), and then vigorously agitating the mixture to cause the sucrose to spontaneously crystallize with the inclusion or entrapment of the active. Thus in this process, crystallization, conglomerate formation, active entrapment, and water volatilization all occur more or less simultaneously within the agitation step making the overall process more difficult to control and optimize.

This difficulty is recognised in Food Technology, 42, 87-90. 1988 where it is stated that the process requires proper control of the rates of nucleation and crystallization, and thermal balance during all of the various phases of the process A similar co-crystallization process for encapsulated orange peel oil is also disclosed in LWT—Food Science and Technology 29, 645-647, 1996. This describes how 100 g to 250 g of orange peel oil can be incorporated per kg of sugar but that, while the product is granular and easy to handle, the flavor oxidizes readily on subsequent storage and addition of an antioxidant is necessary to protect the flavor. The porous structure of the agglomerates apparently leads to flavor oxidation.

Thus, it would be desirable to provide a crystalline encapsulation system which addresses one or more of these drawbacks. It would be especially desirable to increase the ability to control the process more precisely. It would also be desirable to avoid or at least minimise the porosity of the structure so as to better protect labile or sensitive active ingredients.

Other crystalline entrapments systems are also known. For instance, U.S. Pat. No. 2,566,410 (Griffin) describes a process for creating a solidified composition of a continuous crystalline sorbitol phase and a dispersed essential oil phase. The essential oil is described as "so thoroughly coated and entrapped that loss of said oil from the mass occurred at a negligible rate." However, unseeded crystallization of sorbitol is known to be a time consuming process taking up to several days (Szatisz J. Therm. Anal. 12 (1977) 351-360) which is an obvious drawback for any commercial application.

U.S. Pat. No. 2,904,440 (Dimick et al) also relates to sorbitol encapsulation where the water and low molecular weight alcohols are removed from a flavoring agent prior to incorporation in molten sorbitol. This is said to remove constituents that interfere in the crystallization process and extend the use of the technology to other systems such as fruit essences. However, this requires additional steps in the process. Further, the sorbitol melt needs to be supercooled prior to adding flavor and seed crystals. Finally, the solidified product needs to be ground into granular particles.

U.S. Pat. No. 4,388,328 (Glass) employs a mixture of sorbitol, saccharine and mannitol as the entrapping medium. Mannitol and saccharin are believed to lower the crystallization temperature of sorbitol to below 70° C. rendering the process advantageous for incorporating volatile flavor compounds. The melt-emulsion could be cast while liquid as a sheet or formed into tablets or droplets with a mold. To create smaller particles solidified sheets are ground and passed through a mess screen.

Nevertheless, generating particles by grinding inevitably leads to a loss of active ingredient at the surface where ground and so it would be desirable to address this problem.

U.S. Pat. No. 6,083,438 describes a process for preparing a composition suitable for use as an excipient for tabletting comprising following steps of (a) mixing of erythritol and sorbitol in a dry form, (b) heating to a temperature where the mixed products are melted, (c) cooling the product, (d) milling the cooled product to obtain a composition having a desired particle size. Milling suffers from the same drawbacks as grinding.

It is also known to use mannitol, a typically crystalline material, in flavor encapsulation. In U.S. Pat. No. 3,314,803 (Dame et al) acetaldehyde is incorporated into mannitol solids through spray drying a super-saturated solution of mannitol. However, this process requires great care in drying the super-saturated solution to avoid completely volatilizing the acetaldehyde or forming a non-entrapping dried mannitol composition. In EP-A1-0497439, erythritol is spray-dried to provide conveniently sized crystals in the form of a free-flowing powder.

However, in both cases, such heating is potentially detrimental since it encourages the loss of liquid or volatile active ingredients.

It would thus be desirable to address this problem.

Encapsulation of active ingredients by spray chilling is described in U.S. Pat. No. 5,525,367 where the carrier for the active ingredient is a high melting-point edible solid such as a hydrogenated vegetable oil, a stearin, or an edible wax. However, such carriers do not always provide a sufficient barrier to prevent hydrophobic active ingredients from leaking from the capsules.

In US-A1-2009/0142401 (Appel et al) spray-congealing is used to form multiparticles of low-solubility drugs and carriers that result in rapid release of the drug. The carrier may be a sugar alcohol such as mannitol or erythritol, and the particles may be prepared by atomisation. The amount of water needs to be sufficient to dissolve the sugar alcohol and the only numbers disclosed are 60%, 55% and 50% water. This water is driven off by heating which, as identified above, is a critical driver of the loss of the active ingredients.

Thus, it is an object of the present invention to address one or more of the problems and/or to provide one or more of the solutions mentioned above.

SUMMARY OF THE INVENTION

Accordingly, the present invention provides a spray-chilled particulate delivery system, the particulate delivery system having a crystalline structure and comprising (i) a liquid hydrophobic active ingredient and (ii) a carrier material selected from the group consisting of erythritol and mannitol and mixtures thereof, wherein, relative to the total weight of the carrier material, 75% or more of the carrier material is in crystalline form.

The invention further provides a process for preparing a particulate delivery system having a crystalline structure comprising the steps of:
(i) forming a melt of a carrier material selected from the group consisting of erythritol and mannitol and mixtures thereof,
(ii) incorporating a liquid hydrophobic active ingredient into the melt,
(iii) forming a melt-mixture comprising an emulsion, dispersion, solution or suspension of the liquid hydrophobic active ingredient in the melt,
(iv) forming discrete particles of the melt mixture, and
(v) cooling the discrete particles,
so as to form a particulate delivery system in which, relative to the total weight of the carrier material, 75% or more of the carrier material is in crystalline form

DETAILED DESCRIPTION

The delivery system of the present invention comprises a carrier material selected from the group consisting of erythritol and mannitol and mixtures thereof.

These materials have the technical common feature that they are hydrophilic, non-polymeric, that they melt at below a temperature of 190° C. and that, upon solidification, they crystallize rapidly. In this context "rapidly" means that the ratio of the melting temperature of erythritol and/or mannitol to the glass transition temperature of the corresponding alcohol of erythritol and/or mannitol respectively is greater than 1.6. That is, these materials have a significantly higher propensity to form crystals than to form amorphous masses, as is the case for the many sugar alcohols that are unsuitable for use in the present invention.

The delivery system is crystalline. In the context of the present invention, "crystalline" means that, relative to the total weight of the carrier material, 75% or more, more preferably 80% or more, most preferably 90% or more of the matrix or carrier material is in crystalline form. This has the advantage that it is less hygroscopic than, for instance, amorphous delivery systems.

By "in crystalline form" is meant that the matrix comprises crystals that exhibits long-range order in three dimensions and/or that the matrix comprises meso-crystals, as described in the publication (12) Cölfen, H.; Antonietti, M. *Angew. Chem., Int. Ed.* 2005, 44, 5576, i.e. a superstructure of crystalline nanoparticles with external crystal faces on the scale of some hundred nanometers to micrometers. Crystallinity and meso-crystallinity can be measured using known techniques in the art such as powder x-ray diffraction (PXRD) crystallography, scanning electron microscopy, solid state NMR or differential scanning calorimetry (DSC).

The advantage of using a non-polymeric crystalline carrier is that, upon spray-chilling, the carrier will tend to crystallise such that all the molecules occupy defined spaces in the lattice. By contrast, conventional polymeric carriers, such as polyethylene glycol, tend to crystallize in regions along their length, leaving the remainder of the polymer essentially amorphous.

Thus, without wishing to be bound by theory it is believed that the delivery system of the present invention provides a structure in which the active ingredient is not merely entrapped between large crystals (such as macro or microscopic crystals), as is the case in many conventional encapsulation systems, but is, to an increased extent, included within crystals or meso-crystalline domains.

By "included" it is meant that the active ingredient becomes incorporated within a host crystal or meso-crystalline domain as a molecule or droplet. This is in contrast to, for instance, entrapment where the active is concentrated between crystal grain boundaries.

The delivery system is spray-chilled. This provides the advantage that the discrete particles have a reduced tendency to form voids and shell-like structures, such as may occur during conventional spray drying processes.

Further, spray-chilling typically provides a more homogeneous particle size than, for instance, conventional spray drying.

Therefore, a skilled person in the art will be able to ascertain, by looking at the particles, a structural difference from particles produced by other drying techniques.

The carrier materials are selected from the group consisting of erythritol and mannitol and mixtures thereof. Erythritol is most preferred since it is a low molecular weight food grade sugar alcohol that is a stable crystalline material at room temperature and melts at a temperature of 121° C. Its viscosity, as measured by rotational viscometry, is only 24 mPa·s at 130° C., which reduces the energy input required during processing compared to more viscous materials and lowers the associated risk of overheating the sensitive active ingredient.

The freely-settled bulk density of the product comprising the particles of the invention is preferably from 0.7 g cm$^{-3}$ to 1.35 g cm$^{-3}$.

The particle density, i.e. the density of the individual particles, is preferably from 1 g cm$^{-3}$ to 1.45 g cm$^{-3}$.

The delivery system comprises an active ingredient. In the context of the present invention, the phrase "active ingredient" denotes an ingredient, component, mixture of ingredients or the like that it is desired to encapsulate.

The active ingredient is hydrophobic. In the context of the present invention the term "hydrophobic" means that, where the active ingredient is a single compound, it has a c log P greater than 2 and where the active ingredient is a mixture of compounds, 50% by weight or more of the compounds have a C log P higher than 2, more preferably greater than 3. For the purposes of the present invention, C log P is measured using the C log P calculator "EPI Suite version 3, 2000 from the US Environmental Protection Agency.

The active ingredient is preferably present in an amount ranging from about 5% to about 50% by weight, based on the total weight of the delivery system.

It is critical that the active ingredient is hydrophobic since this directly affects the nature of the spray-chilled product and the effectiveness of the encapsulation. By contrast, it is not critical whether the active ingredient is typically for use in, for instance, the flavor and fragrance industry, the pharmaceutical industry, the foods industry, or any other industry since the technical domain does not have a bearing on the successful encapsulation of the active ingredient in the form of a spray-chilled particle.

In one aspect, the solubility of the carrier component, i.e. erythritol, mannitol or mixtures thereof, in a solution of the active ingredient may be less than 10% by weight of the total carrier component at room temperature. If it is more soluble than this then the risk that the delivery system does not form the required crystalline structure is increased.

The active ingredient may be characterised by a Hildebrand solubility parameter smaller than 30 [MPa]$^{1/2}$. The aqueous incompatibility of most oily liquids can be in fact expressed by means of Hildebrand's solubility parameter δ which is generally below 25 [MPa]$^{1/2}$, while for water the same parameter is of 48 [MPa]$^{1/2}$, and of 15-16 [MPa]$^{1/2}$ for alkanes. This parameter provides a useful polarity scale correlated to the cohesive energy density of molecules. For spontaneous mixing to occur, the difference in δ of the molecules to be mixed must be kept to a minimum. The Handbook of Solubility Parameters (ed. A. F. M. Barton, CRC Press, Bocca Raton, 1991) gives a list of δ values for many chemicals as well as recommended group contribution methods allowing to calculate δ values for complex chemical structures.

The hydrophobic active ingredient is liquid at 45° C. and 1 atmosphere. The delivery system of the present invention provides an excellent protection against loss upon storage for such liquid hydrophobic ingredients.

The liquid active ingredient may also be volatile. By "volatile", it is meant that the active ingredient preferably has a vapour pressure of ≥0.007 Pa at 25° C. If the active ingredient comprises a mixture of compounds, preferably at least 10 wt %, based on the total weight of the active ingredient, have a vapour pressure of ≥0.1, more preferably at least 10 wt % have a vapour pressure of ≥1 Pa at 25° C., and most preferably at least 10 wt % have a vapour pressure of ≥10 Pa at 25° C.

For the sake of example, the following non-exhaustive categories of active ingredient are provided. Thus, for instance, the active ingredient may be a flavoring, perfuming or nutraceutical ingredient or composition.

The phrase "flavor or fragrance compound or composition" as used herein, thus defines a variety of flavor and fragrance materials of both natural and synthetic origin. They include single compounds and mixtures. Natural extracts can also be encapsulated in the extrudate; these include e.g. citrus extracts, such as lemon, orange, lime, grapefruit or mandarin oils, or essential oils of spices, amongst other.

The phrase flavor includes not only flavors that impart or modify the smell of foods but include taste imparting or modifying ingredients. The latter do not necessarily have a taste or smell themselves but are capable of modifying the taste that other ingredients provides, for instance, salt enhancing ingredients, sweetness enhancing ingredients, umami enhancing ingredients, bitterness blocking ingredients and so on.

Further specific examples of such flavor and perfume components may be found in the current literature, e.g. in Perfume and Flavor Chemicals, 1969, by S. Arctander, Montclair N.J. (USA); Fenaroli's Handbook of Flavor Ingredients, CRC Press or Synthetic Food Adjuncts by M. B. Jacobs, van Nostrand Co., Inc. They are well-known to the person skilled in the art of perfuming, flavoring and/or aromatizing consumer products, i.e. of imparting an odour or taste to a consumer product.

An important class of oxygen-sensitive active materials that can be encapsulated in the delivery system of the present invention are "oils rich in polyunsaturated fatty acids", also referred to herein as "oils rich in PUFA's". These include, but are not limited to, oils of any different origins such as fish or algae. It is also possible that these oils are enriched via different methods such as molecular distillation, a process through which the concentration of selected fatty acids may be increased. Particularly preferred compositions for encapsulation are nutraceutical compositions containing polyunsaturated fatty acids and esters thereof.

Specific oils rich in PUFA's for use in the present delivery system include eicosapentanoic acid (EPA), docosahexanoic acid (DHA), arachidonic acid (ARA), and a mixture of at least two thereof.

Such oils may, optionally, be supplemented with an antioxidant. For example, the antioxidant-supplemented oil may comprise added ascorbic acid (vitamin C) and/or tocopherol (vitamin E). Tocopherol may be α-, γ-, or δ-tocopherol, or mixtures including two or more of these, and is commercially available. Tocopherols are soluble in oils and may be easily added at amounts in the range of 0.05-2%, preferably 0.1-0.9%, of the supplemented oil comprising the antioxidant.

The delivery system may comprise further optional components. For instance, a carbohydrate such as a monosaccharide, an oligosaccharide, a polysaccharide or any modified form thereof, may be present. It is important that the carbohydrate is not present at a level that would adversely affect the crystalline structure of the delivery system. Thus, in the matrix, any such carbohydrate is present at a level of 5% by weight or less.

An emulsifier may be present in the delivery system. Examples of suitable emulsifiers include lecithin, modified lecithins such as lyso-phospholipids, DATEM, mono- and diglycerides of fatty acids, sucrose esters of fatty acids, citric acid esters of fatty acids, and other suitable emulsifiers as cited in reference texts such as Food Emulsifiers And Their Applications, 1997, edited by G. L. Hasenhuettl and R. W. Hartel.

A viscosity modifier may be present in the delivery system. Examples of suitable viscosity modifiers include ethyl cellulose (e.g. the Ethocel range from Dow Chemicals), hydrophobic silicas and organophilic clay.

Water may be present at very low levels in the matrix. For instance, 10% or less by weight based on the total weight of the matrix, more preferably 7% or less, even more preferably 5% or less, most preferably 2% or less, e.g. 1% or less by weight of water may be present. Such a small amount of water may beneficially lower the melting point of the crystal thereby reducing the temperature to which the active ingredient is subjected. Furthermore, since there is little or no need to remove water from the mixture in preparing the spray-chilled particles, there is a minimal risk of "puffing" due to the evaporation of water. This is a known problem with spray-drying where the water, as it evaporates, can create voids in the particle structure. Thus, the spray-chilled particles of the invention typically have a higher density than corresponding spray-dried particles and so provide for a more compact storage and transportation of the finished product.

Adjuvants such as food grade colorants can also be present so as to provide colored delivery systems.

If desired, an anticaking agent can be present to reduce the risk of the granules from sticking to one another.

The delivery system may be further encapsulated to provide additional benefits. For instance, a barrier material may be coated onto the delivery system, in order to serve as a moisture barrier or an enteric coating. Examples of suitable barrier materials include modified celluloses such as ethyl cellulose, waxes, fats, zein, shellac and the like.

The delivery system according to the present invention comprises particles. The particles can comprise individual crystals or a plurality of crystals. For instance, the particles of the delivery system may comprise a lattice of crystals joined together. Preferably the average particle size, based on the mean diameter, of the granules is from 50 to 4000 microns. The particles are preferably of substantially uniform granulometry.

The process of the invention comprises distinct steps:

(i) Forming a Melt of a Carrier Material Selected from the Group Consisting of Erythritol and Mannitol and Mixtures Thereof This forms a liquid from the continuous phase which is essential so that the flavor or fragrance can be emulsified or dispersed within it.

It is highly desirable that the melting point of the continuous phase is less than 190° C. since this helps to prevent significant degradation of heat labile active ingredients. It is further important to carry out the process at a temperature below the flash point of the active ingredient so that the vapour pressure of the active ingredient is maintained at an acceptably low level.

(ii) Incorporating a Liquid Hydrophobic Active Ingredient into the Melt

This step can be performed by any standard process and the skilled person will readily appreciate suitable methods by which this can be accomplished.

(iii) Forming a Melt-Mixture Comprising an Emulsion, Dispersion, or Suspension of the Melt Preferably the emulsion, dispersion or suspension is formed under conditions in which the product is homogenized. Homogenization is highly advantageous since it reduces the risk of phase separation which, upon solidification, would cause the active ingredient not to be included within the crystalline structure of the carrier material.

Optionally and advantageously, the melt mixture is supercooled. In other words, it is preferably cooled below the melting point of the matrix material but remains in the form of a melt. This allows for the reduction in the vapor pressure of the active ingredient and reduces the amount of heat energy that needs to be removed in the subsequent step.

If an emulsion is formed from the melt, it is preferred that the phase volume of the oil is less than 50%, more preferably less than 40% so as to maintain the emulsion with the oil in the dispersed phase of the emulsion.

The melt-mixture comprises a low amount of water, enabling the formation of the spray-chilled solid without requiring a large amount of water to be driven off. Thus the melt-mixture comprises 10% or less, more preferably 7% or less, even more preferably 5% or less, most preferably 2% or less, e.g. 1% or less by weight of water by weight based on the total weight of the melt-mixture.

(iv) Forming Discrete Particles of the Melt-Mixture

In the context of the present invention, "discrete particles" means particles, droplets or fibres.

The particles are preferably formed by a process that is suitable for low viscosity melts. For instance, the particles may be formed by techniques such as ultrasonic atomization, centrifugal wheel atomization, prilling (break-up of a jet or dripping).

Cutting or chopping is not suitable in the present context since this typically requires high viscosity melts in order to be effective.

The formation is carried out on the melt either above the melt temperature of the matrix or, more preferably, on the supercooled matrix.

Any suitable commercially available apparatus known to the skilled person can be used in this step.

The formation of discrete particles whilst the mixture is in the form of a melt is essential since the minimises the loss of active ingredient from the delivery system, especially when compared to known delivery systems that rely on crushing or grinding a solidified mass to form granules and which allow the loss of active ingredient that is at the surface of the particles where it is ground.

(v) Cooling the Discrete Particles

Cooling of the melt particles formed in the previous step is required to induce crystallisation.

The cooling step is performed rapidly in order to ensure that the active ingredient remains included, to a significant extent, in the developing crystals. For instance, it is desirable that the cooling step comprises heat removal at a rate of greater than about 600 kJ·kg$^{-1}$·min$^{-1}$.

This is advantageous in that it allows the active ingredient to be encapsulated to a greater extent within the developing crystals, resulting in excellent barrier properties upon storage.

To achieve the rapid cooling required according to the present invention, suitable processes include, but are not limited to spray congealing, spray chilling, or melt atomization. Such processes are sometimes referred to generically as prilling. The cooling step can be performed by quenching with a cooling medium, such as a cooling gas or liquid, Inert gases and liquids such as limonene, liquid nitrogen, cooling media air, nitrogen and carbon dioxide are all suitable for this purpose.

Suitable apparatus and processes include cooling of the particles in a cooling tower, fluidized bed or cooled belt or directly in an immiscible fluid.

In the process according to the present invention, the incorporation of the liquid hydrophobic active ingredient, the formation of the discrete particles, and the crystallization processes are achieved in distinct phases or steps of the process. This is in contrast to traditional co-crystallization processes for forming crystalline delivery systems, which involves volatilization of water at the same time as oil incorporation.

Such differences provide the process of the present invention with a more precise control of the nature of the delivery system and reduce the risk of creating channels in the crystalline structure that are a known factor contributing to a porous network by which liquid active ingredients can escape upon storage.

In the process according to the present invention, there is little or no reduction in moisture content during any of the steps. This allows for a more effective inclusion and entrapment of the active and thereby allows improved protection against oxidation.

Further, the delivery system is not subject to a drying step using heat, such as in a spray-drying process, which is often a principle cause of the loss of liquid, hydrophobic active ingredient.

The delivery system can be used to enhance a variety of products. For instance, it can be used in edible compositions such as foodstuffs, pharmaceutical compositions, nutraceutical compositions, oral care compositions, such as chewing-gum or toothpaste, as well as home-care and body-care compositions.

For instance, non-limiting examples where the delivery system finds utility include dry beverages, dry doughs such as cake or bread mixes, cookies, intermediate moisture content foods, stock cubes, powdered laundry detergents, pharmaceutical tablets.

In the case of drug delivery systems, the delivery system of the present invention is particularly useful as it will ensure similar composition and release properties from batch to batch.

If the active ingredient is a flavor oil, it can be advantageously used to impart or modify the organoleptic properties of a great variety of edible products, i.e. foods, beverages, pharmaceuticals and the like. In a general manner, they enhance the typical organoleptic effect of the corresponding unencapsulated flavor material.

Where the active material is an oil rich in polyunsaturated fatty acids or a nutraceutical composition comprising such an oil, it can be provided in any foodstuff where health benefits are desired. In such products, a further advantage of the present delivery system is that it can mask the flavor of the oil rich in polyunsaturated fatty acids, which may not be compatible with the flavor of the foodstuff into which it is incorporated.

The total amount of delivery system in such consumer products can vary across a wide range of values, which are dependent on the nature of the consumer product and that of the particular delivery system of the invention used.

Typical amounts, to be taken strictly by way of example, are comprised in a range of values as wide as from 0.001% to 5 or even 10% of the weight of a flavoring composition or finished consumer product into which they are included.

EXAMPLES

The invention will now be described in further detail by way of the following examples.

Example 1

Preparation of a Delivery System of the Invention

A mixture of 9 parts molten erythritol and 1 part limonene/lecithin solution were poured into a pressurizable vessel and tempered to 130° C. The two fluids were then mixed for 30 seconds using an Ultra Turrax homogenizer to create an emulsion. This emulsion was pushed through a spray nozzle under 60 psi of nitrogen head pressure. The spray broke up into fine melt-emulsion droplets, which then fell onto a room temperature metal tray. Within seconds the droplets hardened forming crystallized solid granules of erythritol containing the dispersed limonene.

Photomicrographs of the granules were taken and showed the oil droplets primarily within the erythritol crystals.

Example 2

Preparation of a Further Delivery System of the Invention

A mixture of 9 parts molten erythritol and 1 part mint flavor (ex Firmenich, Geneva, Switzerland, reference 885106 NT)/lecithin solution was poured into a pressurizable vessel and tempered to 130° C. The two fluids were then mixed for 30 seconds using a Ultra Turrax T25 homogenizer (IKA Works, to create an emulsion. This emulsion was pushed through a 22 gauge needle under 20 psi of nitrogen head pressure forming a liquid jet. After falling a distance of 0.5 m the jet broke up into droplets or prills, which in turn fell into a beaker of chilled limonene. The prills hardened sufficiently fast to avoid coalescence at the bottom of the beaker. The hardened prills were collected and allowed to air dry on a paper towel in order to remove limonene from the surface. This process yielded solid granules that retained the liquid mint flavor.

Example 3

Flavored Chewing Gums with Iso-Loading of Flavor

An unflavored chewing gum base was prepared having the following ingredients in the amounts shown.

TABLE 1

| Ingredient | Amount (wt %) |
|---|---|
| Solsona T Gum Base (1) | 12.44 |
| Vega Gum Base (1) | 12.44 |
| Crystalline sorbitol P60W | 56.50 |
| Maltitol Syrup | 11.50 |
| Glycerin | 6.92 |
| Aspartame | 0.12 |
| Acesulfame K | 0.08 |

(1) ex Cafosa

A Sigma-blade mixer was pre-heated to 45° C.-50° C. and half of the polyols were added. The gum base was pre-heated to 60° C.-65° C. and added to the mixer. Mixing was carried out for approximately 4 minutes. Finally, the remaining polyols, sweeteners and humectants were added and mixing continued for 4 minutes.

The unflavored chewing gum base prepared above was then flavored to provide the following iso-load chewing gum compositions:

TABLE 2

| Component | Sample 1 CONTROL | Sample 2 TEST |
|---|---|---|
| Unflavored Chewing Gum | 99.70 | 96.67 |
| Liquid Mint Flavor (1) | 0.30 | — |
| Mint Encapsulated Flavor (2) | — | 3.33 |

(1) ex Firmenich, Geneva, Switzerland (reference 885106 NT)
(2) prepared in example 2

For the Control, sample 1, the flavor was added and mixing continued for 2 minutes.

For the Test, sample 2, the encapsulated flavor was added and mixing continued for 2 minutes.

The flavored chewing gum was discharged, laminated and cut into sticks or slabs.

Thus, samples 1 and 2 had iso-loading of liquid mint flavor. 6 trained panelists assessed each chewing gum sample for flavor intensity as follows:

Samples were presented blind and following a balanced presentation order. The flavor intensity was evaluated on a scale of 0 to 10 where 0 denotes no flavor and 10 denotes very strong flavor. All panelists found sample 2 significantly stronger than sample 1 (control), with extremely intense impact of mint flavor and stronger mentholic and cooling character.

Example 4

Flavored Chewing Gums with Iso-Dosage of Capsule to Liquid Flavor

Unflavored chewing gum was prepared as described in example 3 and was then flavored to provide the following iso-dosage chewing gum compositions:

TABLE 3

| Component | Sample 1 CONTROL | Sample 3 TEST |
|---|---|---|
| Unflavored Chewing Gum | 99.70 | 99.70 |
| Liquid Mint Flavor (1) | 0.30 | — |
| Mint Encapsulated Flavor (2) | — | 0.30 |

(1) ex Firmenich, Geneva, Switzerland (reference 885106 NT)
(2) prepared in example 2

For the Control sample 1, the flavor was added and mixing continued for 2 minutes. For the Test sample 3, the encapsulated flavor was added and mixing continued for 2 minutes.

The flavored chewing gum was discharged, laminated and cut into sticks or slabs. Thus, sample 3 contains less than one tenth the amount of mint flavor of sample 1. 6 trained panelists assessed each chewing gum sample for flavor intensity as follows: Samples were presented blind and following a balanced presentation order. The flavor intensity was evaluated on a scale of 0 to 10 where 0 denotes no flavor or and 10 denotes very strong flavor. All panelists found sample 3 stronger than sample 1 (control), with significantly higher impact of mint flavor.

What is claimed is:

1. A spray-chilled particulate delivery system comprising a crystal particle having an average diameter of 5 to 4000 microns and wherein the crystal particle comprises (i) a carrier material selected from the group consisting of erythritol, mannitol and mixtures thereof, wherein, relative to the total weight of the carrier material, 75% or more of the carrier material is in crystalline form, (ii) a volatile hydrophobic active ingredient in an amount ranging from about 5% to about 50% by weight, based on the total weight of the delivery system, (iii) lecithin, and (iv) water in an amount of 10% or less wherein the active ingredient is at least partly included within the crystalline form of the carrier material.

2. The delivery system according to claim 1 wherein the carrier material is erythritol.

3. The delivery system according to claim 1, having a freely settled density of 0.7 g·cm$^{-3}$ to 1.35 g·cm$^{-3}$.

4. The delivery system according to claim 1, wherein the active ingredient, before spray chilling, is liquid when measured at 45° C. and 1 atmosphere.

* * * * *